US008167878B2

(12) United States Patent
VanDusseldorp, Sr.

(10) Patent No.: US 8,167,878 B2
(45) Date of Patent: May 1, 2012

(54) BIPOLAR ELECTROSURGICAL PROBE FOR USE WITH CONDUCTIVE IRRIGATION FLUIDS

(75) Inventor: Gregg A. VanDusseldorp, Sr., Valparaiso, IN (US)

(73) Assignee: endoMedical Concepts, Inc., Crown Point, IN (US)

( * ) Notice: Subject to any disclaimer, the term of this patent is extended or adjusted under 35 U.S.C. 154(b) by 770 days.

(21) Appl. No.: 12/208,541

(22) Filed: Sep. 11, 2008

(65) Prior Publication Data
US 2009/0234349 A1 Sep. 17, 2009

Related U.S. Application Data

(60) Provisional application No. 60/971,317, filed on Sep. 11, 2007.

(51) Int. Cl.
*A61B 18/18* (2006.01)
(52) U.S. Cl. .......................................................... 606/48
(58) Field of Classification Search ............... 606/46–50
See application file for complete search history.

(56) References Cited

U.S. PATENT DOCUMENTS 6,391,025 B1 * 5/2002 Weinstein et al. ............... 606/41
2002/0095152 A1 * 7/2002 Ciarrocca et al. ............... 606/48

\* cited by examiner

*Primary Examiner* — Christopher D Koharski
(74) *Attorney, Agent, or Firm* — Hartman & Hartman, P.C.; Gary M. Hartman; Domenica N. S. Hartman

(57) ABSTRACT

An electrosurgical probe configured for cutting or coagulating tissue, and an electrosurgical procedure that employs the electrosurgical probe. The probe includes first and second conductors disposed in a sheath, and first and second electrodes electrically insulated from the sheath and protruding from its distal end. The first electrode is electrically connected to the first conductor to define an active pole of a radio frequency circuit, and configured to perform cutting or coagulation of tissue when the radio frequency current flows to the first electrode. The second electrode is electrically connected to the second conductor, and configured to define a focused ground point in close proximity to the active pole defined by the first electrode so as to complete the radio frequency circuit with the first electrode when a conductive fluid surrounds the first and second electrodes and the radio frequency current flows to the first electrode.

20 Claims, 6 Drawing Sheets

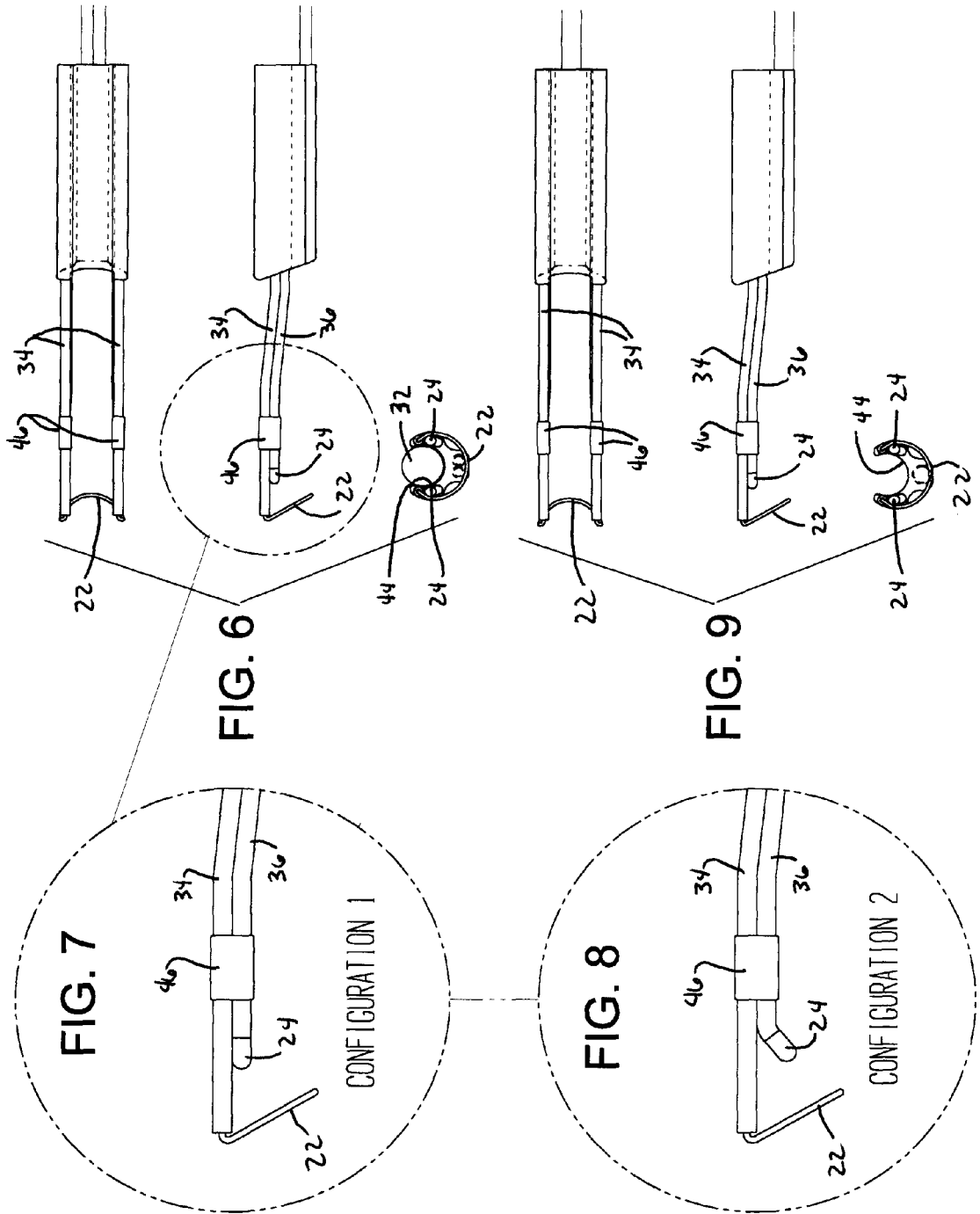

BIPOLAR ELECTROSURGICAL PROBE FOR USE WITH CONDUCTIVE IRRIGATION FLUIDS

CROSS REFERENCE TO RELATED APPLICATIONS

This application claims the benefit of U.S. Provisional Application No. 60/971,317, filed Sep. 11, 2007, the contents of which are incorporated herein by reference.

BACKGROUND OF THE INVENTION

Electrosurgical resection is a procedure in which damaged, diseased or enlarged tissue is removed with an electrosurgical probe. An example is transurethral resection of the prostate (TURP), in which prostate tissue is removed by means of an electrosurgical (electrocautery) probe, for example, a cutting loop that is passed through the urethra by means of a resectoscope. This procedure has served as the historical treatment of benign prostate hypertrophy (BPH) and prostatitus. Another example is endometrial ablation, which is an electrosurgical alternative treatment to hysterectomy in women with menorrhagia (abnormal uterine bleeding). In this case, an electrosurgical probe is passed through the vagina by means of a hysteroscope.

Ablation and resection are electrosurgical effects accomplished by applying a highly damped radio frequency (RF) current to the tissue through an electrode in the form of an active (+) tip of an electrosurgical probe, from which the RF current flows to a second ground (−) electrode. As it passes through tissue from the active tip to the ground electrode, the RF current cuts and/or coagulates the tissue, depending on power and wave length combinations. RF electrosurgical probes are typically equipped with a telescope so that the active tip of the probe is in direct view of the surgeon at all times. RF electrosurgical probes, and particularly their active tips, are available in a number of shapes, sizes, and types, including but not limited to loop (wire), ball tip, roller tip, barrel, cone, point, knife, flat band, coagulating, and punctate electrodes. Examples of a loop electrode suitable for use in TURP and other procedures are represented in FIGS. 1 and 2. In each of FIGS. 1 and 2, RF electrosurgical probes 10 are shown equipped with a loop electrode 12 in which an electrically-conductive U-shaped wire loop is supported between a pair of electrically-conductive arms.

Conventional RF electrosurgical probes (RF probes), such as those commonly used in urological and hysteroscopic resection procedures, are said to be monopolar even though two electrodes are required to complete the RF circuit. FIG. 1 is representative of a monopolar RF probe 10, with the loop electrode 12 of the probe 10 being the active (+) tip of the probe 10, while the other electrode 14 is represented as a patient plate that serves as the ground (−) pole of the RF circuit. The patient plate is typically located on the patients hip or buttocks. The monopolar designation comes from the fact that the probe 10 itself has a single pole. In the circuit described above, the human body becomes a resistive conductor in the negative side of the circuit. This circuit has been used for over eighty years.

Irrigating solutions serve as a coolant for the active tips of RF probes as well as a distention medium to inflate the bladder in urology and the uterus is hysteroscopy. Because the body is not an ideal conductor, it has long been conventional wisdom that only non-conductive irrigation solutions can be used during RF resection procedures, since conductive solutions would dissipate the RF energy and greatly reduce the tissue effect or cutting performance of the probe. In FIG. 1, the use of a non-conductive irrigation solution promotes the flow of RF current from the loop electrode 12, through the tissue 16 being cut, and through the remainder of the human body between the electrode 12 and the ground electrode 14. A commonly-used non-conductive solution is sorbitol ($C_6H_{14}O_6$). The concern of non-conductive irrigation solutions is that they are absorbed by the body during surgery (a process known as intravasation). Too much intravasation during a procedure can result in numerous complications including heat failure, brain damage, etc. The concern for intravasation forces the surgeon to hurry the procedure so as to limit the time that the open wounds are exposed to intravasation of fluids.

Normal saline has no adverse effect on the human body and can even be injected intravenously, and therefore does not have the aforementioned drawbacks of non-conductive irrigation fluids. However, saline is conductive and therefore cannot be used with conventional monopolar RF probes. For example, with reference again to FIG. 1, the use of a conductive irrigation solution causes the RF current to dissipate into the solution from the loop electrode 12, instead of being focused through the tissue 16 to the ground electrode 14.

The desire to use saline irrigation fluids has driven new technology referred to as bipolar electrodes, an example of which is represented in FIG. 2. It is believed that prior art "bipolar" electrodes have often involved simply energizing the metal frame 18 of an otherwise conventional monopolar RF probe 10, such that the metal frame 18 becomes the ground (−) pole of the RF circuit. This in effect moves the ground electrode 14, previously a patient plate located at the patient's hip or buttocks, to a position close enough to the active (+) electrode tip (loop 12) of the probe 10 so that the RF current flows a short distance from the loop 12, through the conductive (saline) solution, to the metal frame 18 of the probe 10. In this manner, loss of RF current by dissipation to the conductive saline irrigation fluid is reduced, and the desired tissue effect or cutting performance of the probe 10 is not significantly degraded.

The use of saline irrigation fluids with bipolar electrodes has been relatively successful, yet has distinct disadvantages. First, using the metal frame 18 of the probe 10 energizes the entire resectoscope or hysteroscope, which could result in burns to the surrounding tissue or the surgeon. For this reason, a patient plate (FIG. 1) may be used in addition to energizing the metal frame 18 to avoid this potential safety issue. Another disadvantage arises because electrical current always searches for the easiest path to ground. In the prior art, because the entire frame 18 of the probe 10 is ground, the RF current does not have a well-focused point to search for.

BRIEF DESCRIPTION OF THE INVENTION

The present invention provides an electrosurgical probe configured for cutting or coagulating tissue, and an electrosurgical procedure that employs the electrosurgical probe to cut or coagulate tissue, for example, in a procedure such as transurethral resection or endometrial ablation.

According to a first aspect of the invention, the electrosurgical probe includes a sheath, first and second conductors disposed in the sheath for carrying a radio frequency current to and from a distal end of the sheath, and first and second electrodes protruding from the distal end of the sheath. The first electrode is electrically insulated from the sheath, electrically connected to the first conductor to define an active pole of a radio frequency circuit, and configured to perform cutting or coagulation of tissue when the radio frequency current flows to the first electrode. The second electrode is electrically insulated from the sheath, electrically connected to the second conductor, and configured to define a focused ground point in close proximity to the active pole defined by the first electrode so as to complete the radio frequency circuit with the first electrode when a conductive fluid surrounds the first and second electrodes and the radio frequency current flows to the first electrode. The probe further comprises a device for passing the radio frequency current through the first conductor, from the first electrode to the second electrode, and through the second conductor without conducting the radio frequency current through the sheath.

According to a second aspect of the invention, the electrosurgical procedure employs the electrosurgical probe described above to cut or coagulate tissue. In a preferred embodiment of the procedure, the electrosurgical probe is inserted into a body cavity, the body cavity is irrigated with a conductive irrigation solution, the radio frequency current is passed through the first conductor, from the first electrode and through the conductive irrigation solution to the second electrode, and then through the second conductor without conducting the radio frequency current through the sheath, and cutting or coagulation is performed on tissue with the first electrode as the radio frequency current flows to the first electrode.

A significant advantage of this invention is the ability to use a conductive irrigation fluid such as a saline solution to irrigate a body cavity when performing an electrosurgical procedure that utilizes radio frequency current. In particular, the second electrode is located in sufficiently close proximity to the first electrode to provide a short path for RF current flow between the first and second electrodes through the conductive irrigation fluid, without the RF current being dissipated in the irrigation fluid to an extent that reduces the ability of the RF current to efficiently cut or coagulate tissue. Furthermore, the first and second electrodes are completely isolated/insulated from the sheath, and therefore do not energize the sheath or a resectoscope or hysteroscope to which the probe is mounted.

Other objects and advantages of this invention will be better appreciated from the following detailed description.

BRIEF DESCRIPTION OF THE DRAWINGS

FIG. 6 depicts top, side, and end views of the electrosurgical probe of FIG. 3.

FIG. 7 is a detailed side view of the electrosurgical probe of FIG. 6.

FIG. 8 is a detailed side view of an electrosurgical probe similar to FIG. 7, but with the second electrode configured in accordance with an alternative embodiment of the invention.

FIG. 9 depicts top, side, and end views of an electrosurgical probe according to another alternative embodiment of the invention.

DETAILED DESCRIPTION OF THE INVENTION

Figure 3:
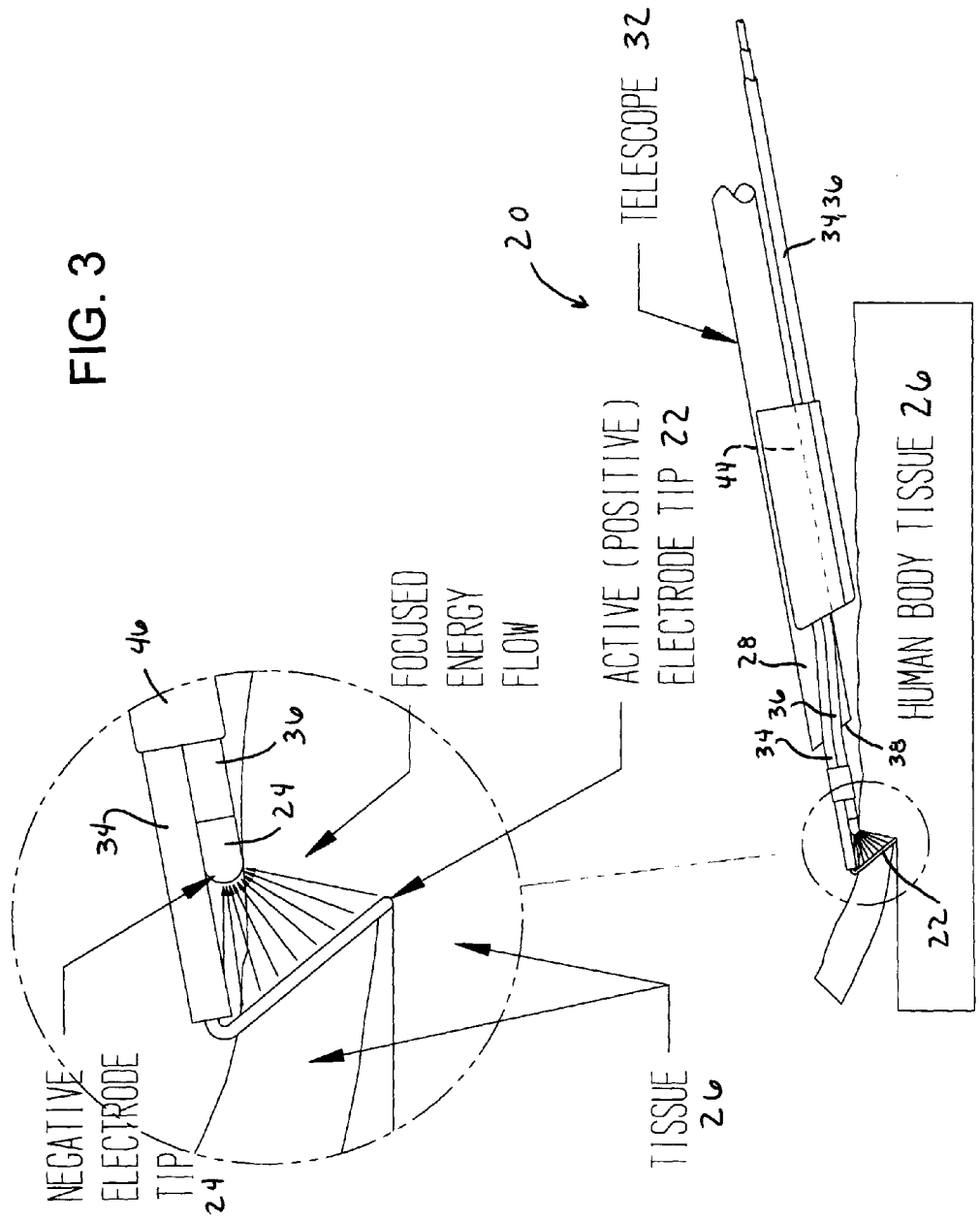
FIG. 3 represents the use of a bipolar RF electrosurgical probe in accordance with an embodiment of this invention, in which the probe is equipped with both a cutting/coagulating electrode that serves as an active (+) tip of the probe and a second electrode that serves as the ground (−) pole of the RF circuit.
Figure 4:
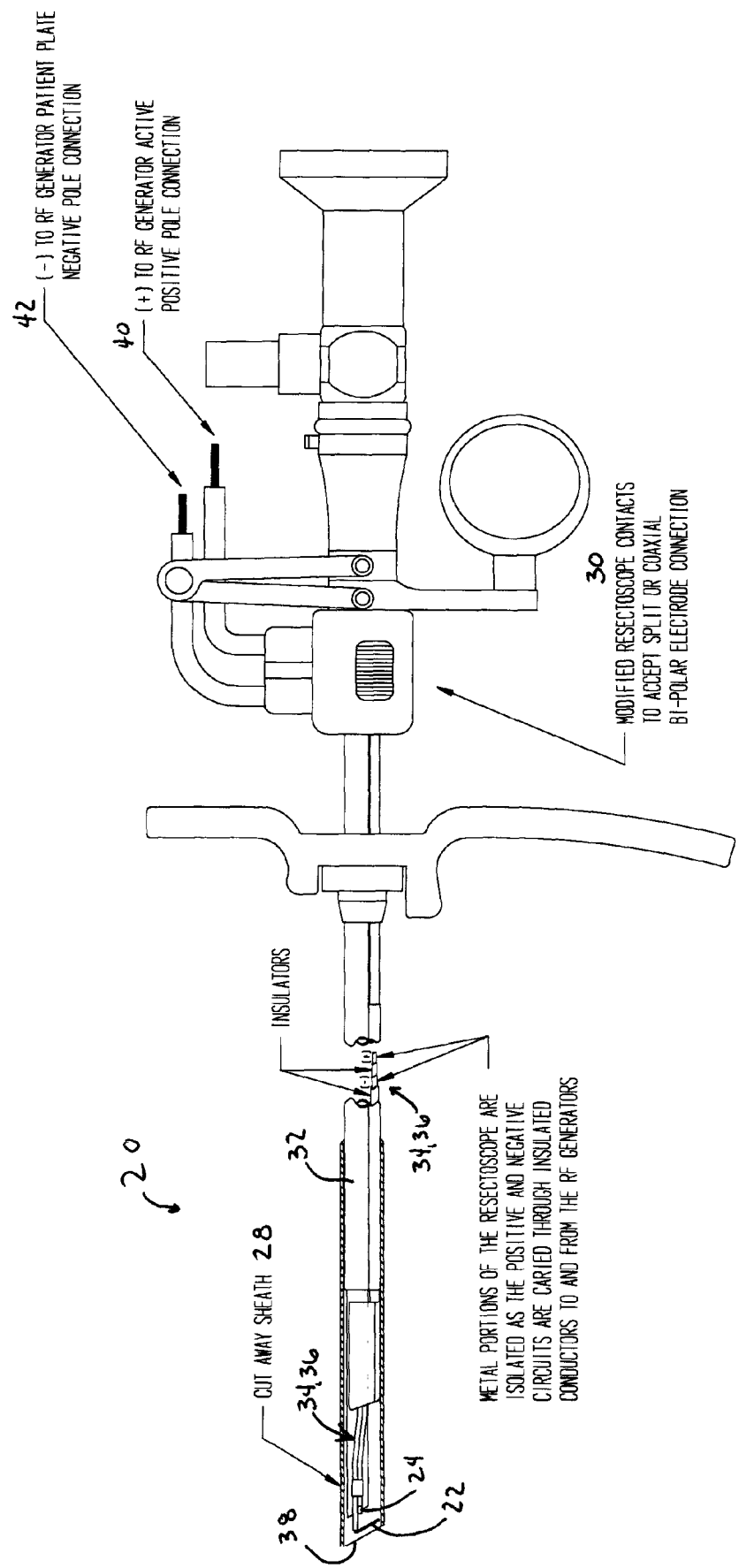
FIG. 4 represents a resectoscope with a sheath shown in partial cross-section to expose the electrosurgical probe of FIG. 3.

FIG. 3 depicts the use of an electrosurgical probe 20 in accordance with a first embodiment of the present invention. FIG. 4 depicts the probe 20 mounted to a resectoscope 30, and FIGS. 5 through 9 depict detailed views and modifications of the probe 20 within the scope of the invention. In FIGS. 3 through 9, consistent reference numbers are used to identify functionally similar structures. While the probe 20 will be discussed in particular reference to electrosurgical procedures such as transurethral resection and endometrial ablation, those skilled in the art will recognize that the probe 20 may have other potential surgical uses.

The probe 20 is represented in FIGS. 3 through 9 as including a sheath 28 through which conductors 34 and 36 are routed between a pair of pole connections 40 and 42 on the resectoscope 30 to a pair of electrodes 22 and 24 at the distal end 38 of the sheath 28. The pole connections 40 and 42 are of a type adapted for connection to an electrosurgical generator (not shown) capable of generating an RF electrosurgical current. As such, the probe 20 can be described as a bipolar RF electrosurgical probe.

The resectoscope 30 can be of any suitable configuration, and various other types of handles could be used in place of the resectoscope 30, including an hysteroscope. The conductors 34 and 36 are insulated from the metal components of the probe 20 and resectoscope 30, including the sheath 28 which may be formed of a metallic material. For this purpose, the conductors 34 and 36 may be coaxial or separate insulated wires. The resectoscope 30 is shown equipped with a conventional pediatric telescope 32 received in a channel 44, allowing direct vision of the probe 20 during placement and during procedures performed with the probe 20. Materials known and used for prior art electrosurgical instruments can be used to fabricate the probe 20, resectoscope 30, and their components.

Figure 5:
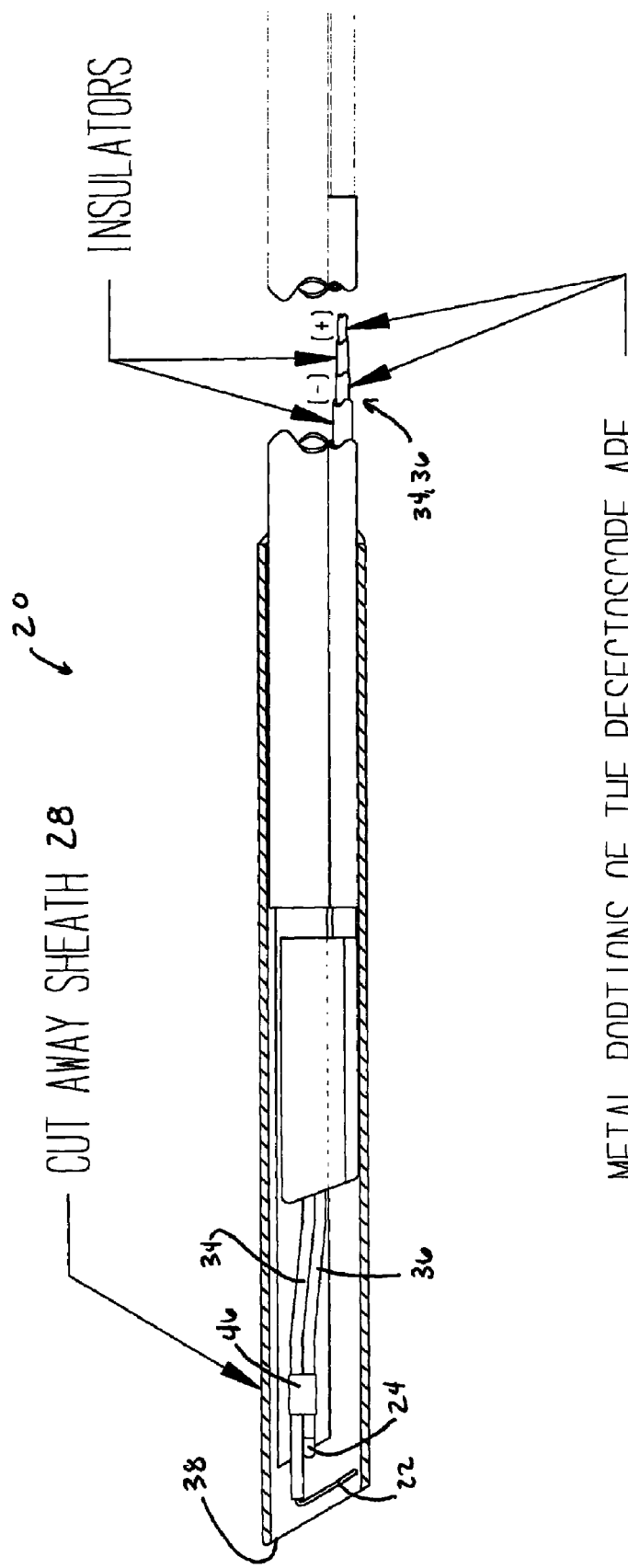
FIG. 5 is a detailed side view of the partial cross-section of the sheath shown in FIG. 4.

As evident from FIGS. 4 and 5, the electrodes 22 and 24 and their conductors 34 and 36 are adapted to be distally extended outside the distal end 38 of the sheath 28. For example, the electrodes 22 and 24 and their conductors 34 and 36 may be capable of reciprocal movement within the sheath 28 through the operation of an actuation lever of the resectoscope 30. The sheath 28 may define an internal flow channel to enable an irrigation fluid to be delivered for immersion cooling of the electrodes 22 and 24, and optionally to inflate the body cavity into which the probe 20 is placed and used, for example, a bladder in a urological procedure or the uterus in an hysteroscopic procedure.

The electrodes 22 and 24 of the probe 20 are electrically connected to their conductors 34 and 36 to define active (+) and ground (−) poles of an RF circuit. In FIGS. 3 through 9, the electrode 22 is configured as a cutting loop (wire), though other configurations are possible and within the scope of this invention, such as such well-known types as ball tip, roller tip, barrel, cone, point, knife, flat band, coagulating, and punctate electrodes. As is generally conventional, the opposite arms of the loop electrode 22 can be individually connected to separate wires connected to the conductor 34, such that the entire electrode 22 is at the same electrical potential. For example, in FIGS. 6 and 9 the conductor 34 is depicted as comprising two separate wires connected to each side of the electrode 22. The loop electrode 22 is represented in FIGS. 3 through 9 as inclined proximally toward the sheath 28 to facilitate the engagement of the tissue 26 during the cutting or coagulation procedure performed with the electrode 22. Suitable materials for the electrode 22 include tungsten and stainless steels, though it is foreseeable that other materials could be used.

Figure 1:
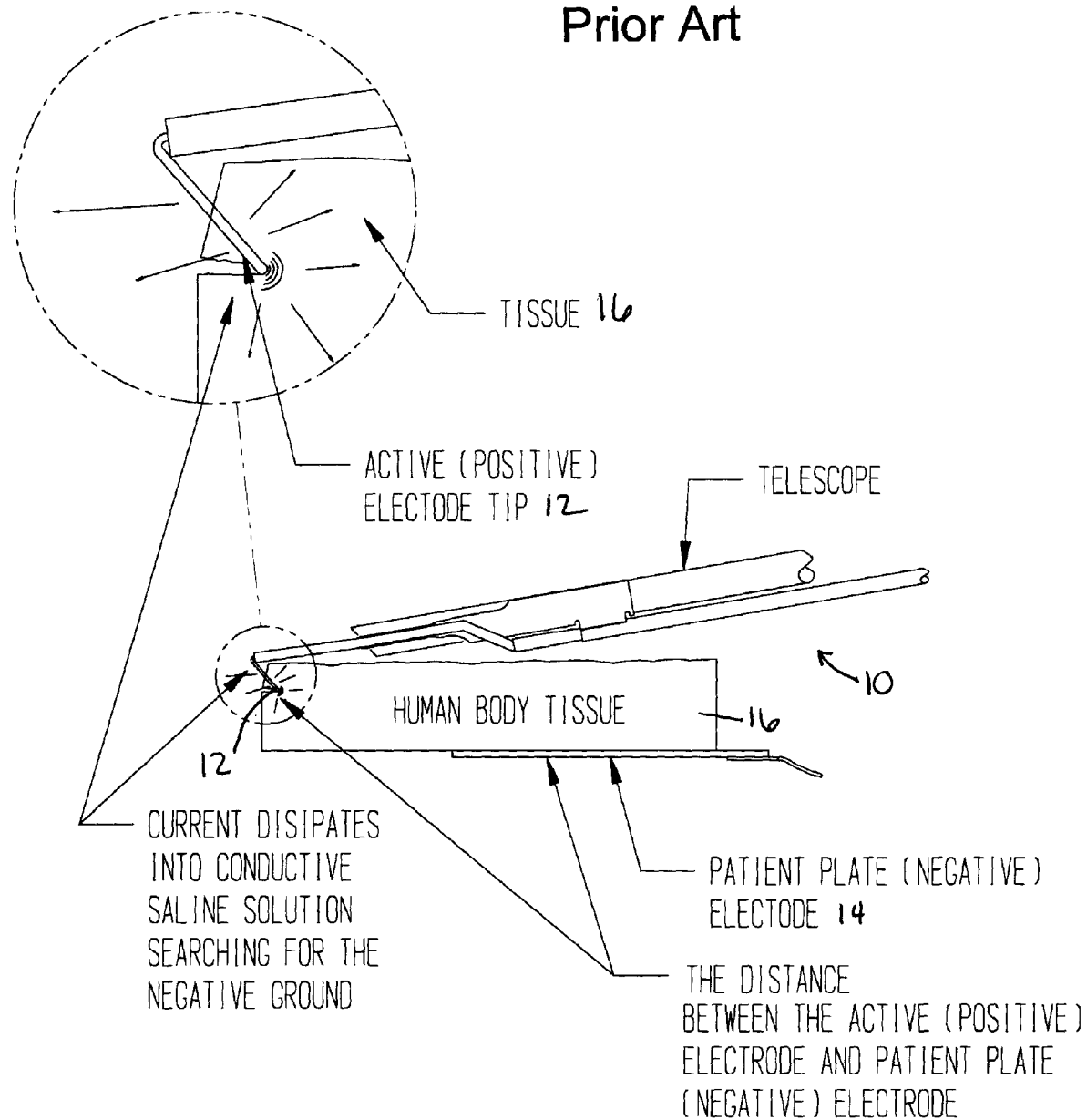
FIGS. 1 and 2 represent the use of monopolar and bipolar RF electrosurgical probes in accordance with the prior art.
Figure 2:
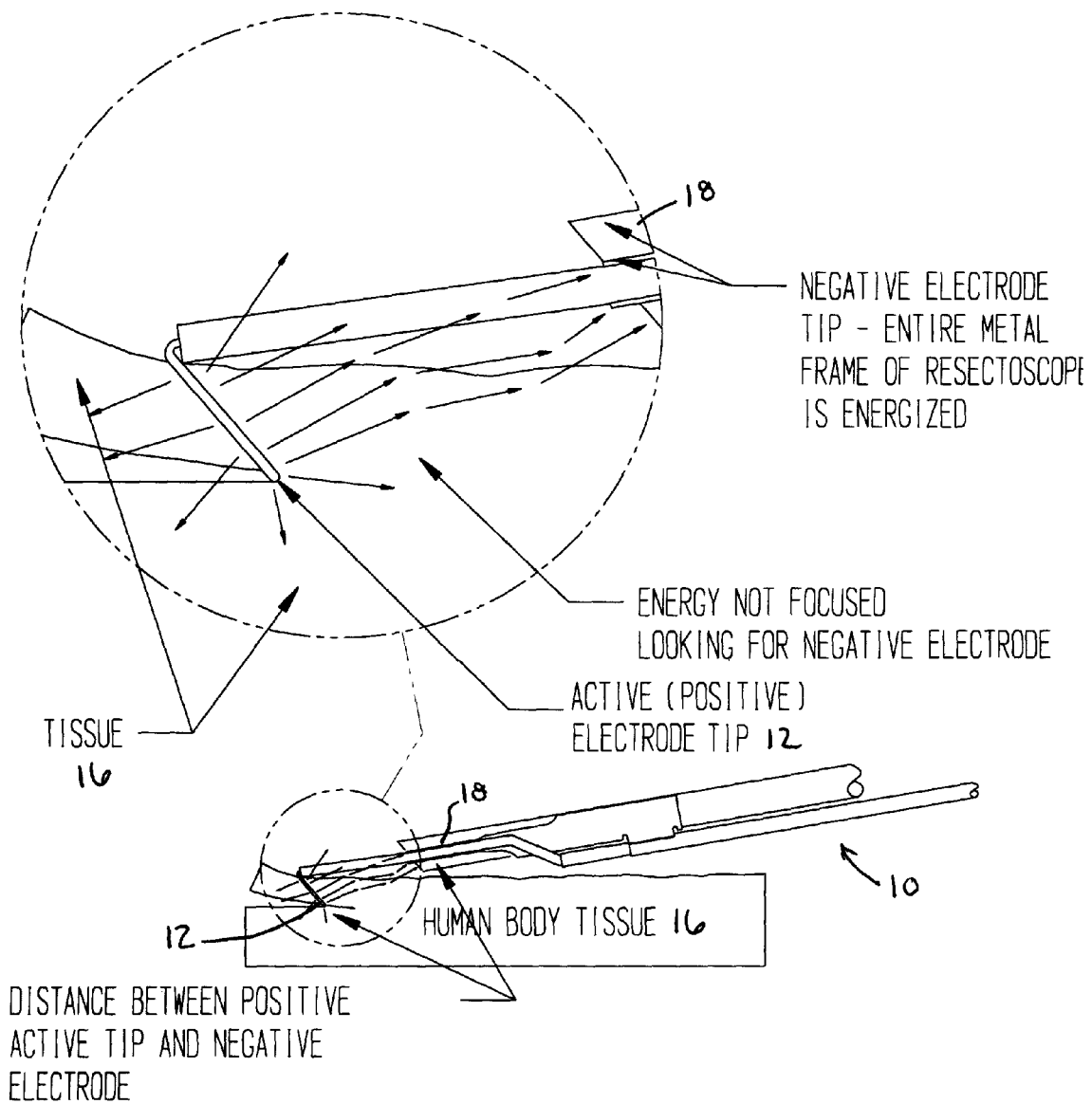

In FIGS. 3 through 9, the second electrode 24 is configured as a cap or post that may be crimped to the end of its conductor 36 so as to be disposed entirely between the first electrode 22 and its conductor 34. In FIGS. 6 and 9, the second electrode 24 is represented as a pair of electrodes 24, each aligned with one of the wires connected to the arms of the loop electrode 22, in which case the conductor 36 preferably comprises two separate wires connected to each electrode 24, so that each electrode 24 is at the same electrical potential. Ferrules 46 are shown in FIGS. 6 and 9 as securing one wire of each conductor 34 and 36 in pairs. Whether the probe 20 is equipped with a single or pair of electrodes 24, each electrode 24 is in close proximity to the loop electrode 22 as evident from FIG. 3, to the extent that during the cutting procedure depicted in which the electrode 22 is completely immersed in human tissue 26, the electrodes 22 and 24 are separated by only the resected tissue 26 and any irrigation fluid in which the tissue 26 and the electrodes 22 and 24 are immersed. According to a preferred aspect of the invention, because of the proximity of the electrode 24 to the distal tip of the loop electrode 22, the irrigation fluid is permitted to be a common saline solution or another electrically conductive solution without unduly dissipating the RF current into the irrigation fluid. The gap width between the electrodes 22 and 24 may be about 0.5 cm or less, but in any event is less than the distance between the loop electrode 22 and the distal end 38 of the sheath 28. The size and shape of the electrode 24, which is more compact than the sheath 28, also helps to provide a stronger focus point for the RF current flowing from the loop electrode 22, further enhancing the performance of the probe 20. The proximity of the electrode 24 can eliminate the need for a patient plate used in the prior practice represented in FIG. 2, though a patient plate may still be used with this invention as a redundant safety ground.

FIG. 6 depicts top, side, and end views of the probe 20 of FIGS. 3 through 5, and FIG. 7 is a detailed view of the configuration of the electrode 24 shown in FIGS. 3 through 6. FIG. 8 represents a slightly modified electrode 24, which instead of extending coaxially from its conductor 36, extends obliquely (for example, about forty-five degrees) from its conductor 36 toward the distal tip of the loop electrode 22. FIG. 9 represents views similar to those shown in FIG. 6, but with the telescope 32 omitted from the channel 44.

While the invention has been described and illustrated in terms of specific embodiments, it is apparent that other forms could be adopted by one skilled in the art. For example, the probe 20 could differ in appearance and construction from the embodiments shown in the Figures, and appropriate materials could be substituted for those noted. Accordingly, it should be understood that the invention is not limited to the specific embodiments illustrated in the Figures. Instead, the scope of the invention is to be limited only by the following claims.

The invention claimed is:

1. An electrosurgical probe for cutting or coagulating tissue, the electrosurgical probe comprising:
    a sheath;
    first and second conductors disposed in the sheath and carrying a radio frequency current to and from a distal end of the sheath;
    a first electrode protruding or adapted to extend from the distal end of the sheath so as to define a distance between the first electrode and the distal end of the sheath, the first electrode being electrically insulated from the sheath, electrically connected to the first conductor to define an active pole of a radio frequency circuit, and configured to perform cutting or coagulation of tissue when the radio frequency current flows to the first electrode;
    a second electrode protruding or adapted to extend from the distal end of from the sheath, the second electrode being attached to a distal end of the second conductor and disposed entirely between the first conductor and the first electrode to define a gap with the first electrode that is less than the distance between the first electrode and the distal end of the sheath, the second electrode being electrically insulated from the sheath, and configured to define a focused ground point in close proximity to the active pole defined by the first electrode so as to complete the radio frequency circuit with the first electrode when a conductive fluid surrounds the first and second electrodes and the radio frequency current flows to the first electrode; and
    means for passing the radio frequency current through the first conductor, from the first electrode and through the gap to the second electrode, and through the second conductor without conducting the radio frequency current through the sheath.

2. The electrosurgical probe according to claim 1, wherein the first electrode is a type chosen from the group consisting of loop, ball tip, roller tip, barrel, cone, point, knife, flat band, coagulating, and punctate electrodes.

3. The electrosurgical probe according to claim 1, wherein the first electrode is inclined proximally toward the sheath.

4. The electrosurgical probe according to claim 1, wherein the first and second conductors comprise separate insulated wires that separately protrude from the distal end of the sheath.

5. The electrosurgical probe according to claim 4, wherein the first and second conductors protrude in parallel from the distal end of the sheath.

6. The electrosurgical probe according to claim 5, wherein the second electrode extends coaxially from the second conductor.

7. The electrosurgical probe according to claim 5, wherein the second electrode extends obliquely from the second conductor and away from the first conductor toward a distal tip of the first electrode.

8. The electrosurgical probe according to claim 1, wherein the sheath is formed of an electrically conductive material.

9. The electrosurgical probe according to claim 1, wherein the electrosurgical probe is coupled to a resectoscope.

10. The electrosurgical probe according to claim 1, wherein the electrosurgical probe is coupled to a hysteroscope.

11. An electrosurgical procedure employing the electrosurgical probe of claim 1 to cut or coagulate tissue.

12. The electrosurgical procedure according to claim 11, the procedure comprising:
    inserting the electrosurgical probe into a body cavity;
    irrigating the body cavity with a conductive irrigation solution;
    passing the radio frequency current through the first conductor, from the first electrode and through the conductive irrigation solution to the second electrode, and then through the second conductor without conducting the radio frequency current through the sheath; and
    performing cutting or coagulation of tissue with the first electrode such that the tissue is between and contacted by the first and second electrodes as the radio frequency current flows to the first electrode and then through the tissue to the second electrode.

13. The electrosurgical procedure according to claim 12, wherein the first electrode is a type chosen from the group consisting of loop, ball tip, roller tip, barrel, cone, point, knife, flat band, coagulating, and punctate electrodes.

14. The electrosurgical procedure according to claim 12, wherein the first electrode is inclined proximally toward the sheath.

15. The electrosurgical procedure according to claim 12, wherein the first and second conductors comprise separate insulated wires that separately protrude from the distal end of the sheath.

16. The electrosurgical procedure according to claim 15, wherein the first and second conductors protrude in parallel from the distal end of the sheath.

17. The electrosurgical procedure according to claim 16, wherein the second electrode extends coaxially from the second conductor.

18. The electrosurgical procedure according to claim 16, wherein the second electrode extends obliquely from the second conductor and away from the first conductor toward a distal tip of the first electrode.

19. The electrosurgical procedure according to claim 12, wherein the procedure is a transurethral resection procedure.

20. The electrosurgical procedure according to claim 12, wherein the procedure is an endometrial ablation procedure.

* * * * *